(12) United States Patent
Loeschinger

(10) Patent No.: US 9,610,028 B2
(45) Date of Patent: Apr. 4, 2017

(54) METHOD AND APPARATUS FOR SENSING A HORSE'S MOODS

(75) Inventor: Juergen Loeschinger, Tuebingen (DE)

(73) Assignee: XYBERMIND GMBH, Tuebingen (DE)

( * ) Notice: Subject to any disclaimer, the term of this patent is extended or adjusted under 35 U.S.C. 154(b) by 981 days.

(21) Appl. No.: 13/878,098

(22) PCT Filed: Sep. 22, 2011

(86) PCT No.: PCT/DE2011/075230
§ 371 (c)(1),
(2), (4) Date: Apr. 5, 2013

(87) PCT Pub. No.: WO2012/048704
PCT Pub. Date: Apr. 19, 2012

(65) Prior Publication Data
US 2013/0211773 A1  Aug. 15, 2013

(30) Foreign Application Priority Data

Oct. 6, 2010 (DE) .................. 10 2010 038 028

(51) Int. Cl.
*A61B 5/11* (2006.01)
*A61B 5/16* (2006.01)
*G01B 7/14* (2006.01)
*G01P 13/00* (2006.01)

(52) U.S. Cl.
CPC ............ *A61B 5/11* (2013.01); *A61B 5/1121* (2013.01); *A61B 5/165* (2013.01); *G01B 7/14* (2013.01); *G01P 13/00* (2013.01); *A61B 2503/40* (2013.01)

(58) Field of Classification Search
CPC ...................................................... A61B 5/165
See application file for complete search history.

(56) References Cited

U.S. PATENT DOCUMENTS

| 5,138,550 | A | 8/1992 | Abraham et al. |
| 6,952,912 | B2 | 10/2005 | Lambert |
| 7,467,603 | B2 | 12/2008 | Davies |
| 2010/0030036 | A1* | 2/2010 | Mottram ............... A01K 11/00 600/301 |

(Continued)

FOREIGN PATENT DOCUMENTS

| DE | 19834257 A1 | 2/2000 |
| DE | 19834257 C2 | 8/2002 |

(Continued)

OTHER PUBLICATIONS

Griffin, Ashley. "Horse Body Language." eXtension. N.p., Sep. 24, 2009. Web. Jan. 25, 2016.*

(Continued)

*Primary Examiner* — John Breene
*Assistant Examiner* — Jeffrey C Morgan
(74) *Attorney, Agent, or Firm* — Lucas & Mercanti, LLP

(57) ABSTRACT

In a method for sensing a horse's moods, in which multiple sensors sense physical parameters of the horse and a statement on the horse's well-being is derived from said measured values, the position of at least one ear is sensed by a sensor, and a statement reflecting the horse's mood in a differentiated manner on the basis of body language-related signals is output.

10 Claims, 3 Drawing Sheets

(56) References Cited

U.S. PATENT DOCUMENTS

2010/0111359 A1* 5/2010 Bai .................. G06K 9/00335
382/103

FOREIGN PATENT DOCUMENTS

| GB | 2437250 A | 10/2007 |
|----|-----------|---------|
| WO | 2004084624 | 10/2004 |
| WO | 2006053290 | 5/2006 |
| WO | 2009058004 A | 5/2009 |

OTHER PUBLICATIONS

Carole Fureix et al: "What do ears 1,3-6,8, positions tell us about horse welfare?", Proceedings of the 45th Congress of the International Society for Applied Ethology (I SAE) : Scientific Evaluation of Behavior, Welfare and Enrichment, Jul. 31-Aug. 4, 2011, Indianapolis, USA, 2011, p. 35, XP55025463.

A. Berger et al: "Evaluation of living conditions of-free-ranging animals by automated chronobiological analysis of behavior", Behavior Research Methods, Instruments, & Computers, vol. 35, No. 3, Aug. 1, 2003 (Aug. 1, 2003), pp. 458-466, XP55025429.

S.J. Hobbs et al: "Motion analysis and its use in equine practice and research", Wiener Tierärztliche Monatszeitschrift, vol. 97, Jan. 1, 2010 (Jan. 1, 2010), pp. 55-64, XR55025423.

\* cited by examiner

METHOD AND APPARATUS FOR SENSING A HORSE'S MOODS

CROSS-REFERENCE TO RELATED APPLICATIONS

This application is a 371 of PCT/DE2011/075230 filed Sep. 22, 2011, which in turn claims the priority of DE 10 2010 038 028.8 filed Oct. 6, 2010, the priority of both applications is hereby claimed and both applications are incorporated by reference herein.

BACKGROUND OF THE INVENTION

Field of the Invention

The present invention relates to a method for capturing a horse's moods.

Description of Prior Art

It is known from U.S. Pat. No. 5,138,550 A to capture the gait of a horse by means of motion sensors attached to the horse's body so that gait abnormalities can be detected.

It is also known from U.S. Pat. No. 7,467,603 B2 to capture motion dependent parameters by sensors attached to the horse's body, so that based on the insights gained thereof concerning the equine motility the horse itself and/or its jockey can be protected from injury or that the horse can be identified by means of the captured data.

It is known from WO 2006/053290 A2 to capture the relationship between breathing and movement of a horse by means of motion sensors attached to the horse's body, in which an accelerometer captures the movements of the equine respiratory system caused by breathing.

It is known from WO 2004/084624 A1 to judge the fitness of a horse by relating data concerning the equine circulatory system with positional information data, such that for example the speed of a horse is detected in a GPS-assisted manner and compared with synchronously captured physiological data of the horse, such as heart rate, blood pressure, body temperature, or the like.

U.S. Pat. No. 6,952,912 B2 also suggests analyzing equine respiration by capturing breathing sounds. Anomalies of the respiratory ducts or else the athletic potential of the horse are thus to be recognized. The sensors are configured in order to allow the elimination of perturbations by ambient noise like wind, hooves or the like.

With an aim slightly different from the previously mentioned publications, which deal with the assessment of the equine physical status, DE 198 34 257 C2 suggests a method for monitoring an animal and in particular a horse, in which different parameters are also captured by means of sensors attached to the horse's body. Reference values of the respective parameters, which are compared to the captured current measurements are stored in the measurement devices used therefore. According to DE 198 34 257 C2, however, it is also possible, in contrast to the previously mentioned publications, to obtain statements concerning the well-being of the horse in addition to purely physiological statements like the equine movements or perspiration, thus this publication describes a generic method.

SUMMARY OF THE INVENTION

An object of the present invention is to improve a generic method in such a way that by monitoring a horse's mood a statement concerning its living and keeping conditions, respectively, can be made, in order to improve these conditions if necessary.

The object is achieved by the present invention by making a differentiated statement concerning at least two different moods of the horse, such that not only the behavior of the horse during training or during a performance but the horse's living conditions in general can be judged. While DE 198 34 257 C2 suggests a quantitative differentiation of a single qualitative criterion—thus of a single mood only—allowing in particular the two statements "the horse feels well" or "the horse doesn't feel well" concerning the well-being, according to the methods disclosed herein statements are made concerning at least two qualitatively different moods of the horse. Examples for these different moods are anxiety, tiredness, aggression, tension vs. relaxedness, interest vs. disinterest, or anger, where the method allows for a quantitative statement concerning each of these.

Converting sensor data into moods is accomplished in several steps. In a first step the different body language-related signals must be recognized by means of the sensor data. Depending on whether a static body language-related signal (e.g. ear position) or a dynamic body language-related signal (e.g. twitching of the ears) is dealt with, different methods are being employed. Each of the recognized body language-related signals is then quantified according to its respective characteristic. In a further step of processing these values are converted into detailed emotions and tempers. More general statements such as the well-being are calculated from these individual moods, as disclosed in more detail below.

Concerning a particularly preferred embodiment of the disclosed method the present invention assumes that the position of the ears and/or the tail can very well express a horse's mood—thus the complex mixture of several individual moods such as the above mentioned anxiety, tiredness and the like.

When the ears are in a standard position, i.e. pricked up and in an orientation laterally slightly pointed to the front, one can assume that the horse is in a relaxed state.

When the horse perceives a noise, it will turn one or both ears in the direction of the noise, so that this re-positioning or movement of the ears can indicate that the horse is in a mood which can be judged as "attentive".

When the horse detects a disturbing noise, it will cock its ears and if applicable the head or the whole body of the horse turns towards the respective direction of the noise. By arranging additional sensors, this body or head movement can be captured and, if desired, also the orientation of the horse in a space can be captured, such that a statement concerning the respective disturbance, which characterizes the horse's mood, can be provided as output.

If the ears are drooping down to the sides in a relaxed manner this suggests that the horse dozes and is relaxed or impassive.

If the ears hang down floppily the horse is likely to feel pain.

If the ears are cocked and pricked up stiffly and in addition they twitch or flutter the horse is in panic.

If the ears are flattened back on the head the horse demonstrates aggression or dominance.

Just by capturing the ear position with sensors a comparatively differentiated statement concerning the horse's mood by means of the body language-related signals mediated by the ears.

In the simplest case one sensor can be used on one ear if one assumes that both ears are always moved synchronously. Preferentially, however, the movements of both ears are captured by using an individual sensor for each ear.

The sensor can be configured as removable ear clip or as permanently attached ear mark. In particular it can preferably be integrated in an ear protector as already well known and commercially available in horse riding.

Preferably, another sensor is provided which is positioned close to the ear on the head of the horse, in order to capture the position of the ears correctly and to avoid errors in the evaluation of the ear movements by underlying head movements so that by comparing both movements the position of the ear on the head can be calculated precisely.

If the ear sensor is already positioned in an ear protector, this ear protector can be configured such that it also covers a region of the horse's head close to the ear so that the above mentioned second sensor close to the ear can be positioned in this part of the ear protector which does not move with the ear but remains in a fixed position on the head.

As known in the art several known ways are available for storage and evaluation of the measurements and the display of the statement concerning the horse's mood can also be achieved in several ways as known in the art.

The computational processing of the measurements captured by one or several sensors can for example be done directly in the device which is positioned on the horse or it can be done on a central server to which they are transmitted. This transmission can be immediate, in particular in a wireless manner, such that the statement concerning the current emotional state of the horse can be provided in almost real time. Alternatively the transmission of the measurements can be done in such a way that these data are first stored intermediately in a device positioned on the horse and read out later, wherein this reading out can be done in a wireless manner as well or in such a way that the above mentioned device is connected by electric contacting such as a USB cable connection to a readout device such as a PC.

Evaluating the measurements can be done in the receiving device itself, for example if this is a PC on which a corresponding evaluating program is running, or the measurements can be further transmitted from the receiving device to a computer, on which a software program as is running an expert system for evaluating the measurements, where said expert system can be far away from the respective horse by internet connection, for example in another city, another country or another continent.

The output of the statement concerning the horse's mood can be provided locally, for example at the site of the server which evaluates the measurements, such as a stable. Alternatively or in addition the output of the statement concerning the mood can be transferred, however, for example as email or as text message to the horse owner, the horse trainer, the veterinarian, the stable owner or the like, where this statement can for example be displayed on a PC or on a mobile device.

The statement concerning the horse's mood can reflect the current emotional state of the horse. Alternatively or in addition a statement can be provided concerning the mood over a certain time interval, for example for a full day or for a week, a month, half a year or the like. This statement can be provided as output in concentrated form of a so called "top level mood", thus in a single statement like "very well", "well", "satisfactory", "fair" or "bad", wherein this summarized, concentrated statement comprises the most diverse moods which were captured in a differentiated manner, in a way that integrates over the specific time interval and accounts for a weighting of these different moods. This will be explained in more detail in reference to FIG. 3.

As an alternative to this summarized statement the statement that was made concerning a specific time interval can be provided as output in a manner that differentiates for the various moods, such that it can for example be indicated which period of time a specific mood has occupied in this chosen time interval. This will be explained in more detail in reference to FIG. 2.

It can be provided to display this statement concerning the mood or the several different moods, respectively, during the time interval not just in one block, as a result, but as course of time during the time interval. In that way one can for example recognize that at certain time points the horse's mood is particularly positive or particularly negative, for example in contact with other horses, in contact with a horse keeper or trainer, at feeding time or upon similar environmental influences, so that specific measures can accordingly be taken in order to minimize negative moods of the horse.

To obtain a statement concerning the horse's mood is of interest for many groups of people:

The horse owner for example frequently spends the major part of the day far away from his horse and accordingly checking the horse and its mood is time consuming. With the help of the disclosed method his horse's mood can also be displayed over large distances to a horse owner, so that the horse owner can for example see how his horse is currently doing.

If the horse is used for sports activities, it is known that for example the stress level directly influences the horse's performance. Accordingly, the performance can be improved by eliminating negative influences, which influence the horse's mood in a negative way, which is in the interest of the horse trainer.

For the stable in which the horse is boarded the disclosed method offers the possibility to document the quality of the horse's accommodation. In particular the possibility is provided to make modifications in the boarding of the horse, for example to let the horse go grazing in a specific group with other horses or to reduce other influences recognized to be negative for the horse or to enhance positive influences, respectively.

For the veterinarian the disclosed method offers the possibility to recognize diseases as early as possible such as lameness of the horse or colics or to monitor or to document, respectively, the healing process of the horse following a disease or during treatment, respectively.

Apart from the significance which is attributed to the position of the horse's ears, the position and the movement, respectively, of the tail can preferably be captured as well. The higher the tail is carried, the more alert the horse. This may stand for activity and zest in a positive sense, but possibly also for aggressiveness in a negative sense. The limper the tail hangs, the stronger the horse feels tiredness, fatigue, anxiety or pain. For example, the following positions or movements, respectively, of the tail can be distinguished: If the tail is lowered, the horse feels subservience, tiredness or weakness. If the tail is pressed to the body, however, the horse feels fear. If the tail stands up, the horse's mood is aggressive or strained. When there are laterally beating tail movements, the horse is tensed, for example because it is distressed or feels pain. Vigorous beating of the tail indicates that the horse is angry.

In addition to the sensors that are used to capture the position of the ears or the tail, respectively, or the associated movements, respectively, further sensors may be provided. These may, for example, capture the overall posture of the horse or the position or movement, respectively, of individual limbs of the horse. Or they can be used to capture the orientation of the horse in a predetermined space or in relation to other horses, so that for example it can be detected if a horse assumes a locking position, thus aligns at an angle of about 90 degrees to the direction of movement of another horse and impedes its movement, because by this body lock the horse shows its dominance over the other horse, so that in this way disturbance or stress in the participating horses arises.

In addition, depending on the sensors used, movements of the individual body parts and also movements of the entire horse can be detected, such as the respective gait of the horse, so that it is possible to capture whether the horse is lying, standing, sleeping, performing slight movements, feeding or drinking, and whether it moves in walk, trot or canter.

Deviations from normal behavior can be recognized if the collected data concerning the horse are stored and analyzed statistically.

The current stress state of the horse can be detected by means of the above mentioned position of the ears and possibly additionally supported by a heart rate or respiratory rate measurement.

The health status of the horse can be captured with high confidence via measurements done in a regular fashion, for example by capturing the gait symmetry, the respiration and other such parameters of the horse.

If the horse is in a pasture or paddock, respectively, and comes in contact with other horses, emerging stress may be signaled for example that can indicate rank struggles within the group or colic or the like.

The captured moods can lead to very differentiated alphanumeric evaluations, for example by transmitting prepared texts as a result of the analysis or by displaying the mood as a number, which, for example, corresponds to a scale value on a mood scale ranging from "excellent" to "very bad".

Instead of the above mentioned alphanumeric scale value that is displayed this value can also be shown in an analog way, for example by means of a pointer that points to a specific section of a scale.

Or captured moods can be displayed graphically in a kind of course chart, block chart, bar diagram or the like.

In the simplest case they can show by a color code, whether, for example, the horse is well (indicated by a green color) or bad (red) or whether the horse is neither doing particularly well nor particularly bad, which may be indicated by yellow coloring. In this way it is either possible to make a particularly clear and simple statement concerning the horse's mood that is easily readable for laymen, or it is possible, in particular with the concurrent display of the moods of a variety of horses, to display in a readily understandable way for example in the stable or in an animal hospital, how the individual animals are and what the general mood in the stable is, because, through the predominant color impression, it is understandable for all animals at the same time and virtually "at a glance". With such a simplified and quickly comprehensible representation of the horses' moods, in which the color code indicates red, for example, the corresponding keepers can either go to the animals or retrieve a detailed analysis of the horse in order to find out in this way greater detail what the current problems of the horse are.

The horse is a herd animal and communicates largely through its body. The body language-related signals emitted by the horse can be dynamic as well as static, i.e. they can be given both by the position of individual body parts or by the posture of the entire body, respectively, as well as by the corresponding movements. Individual body parts are of different importance here. By appropriate sensoric capturing of the horse's physiological parameters, therefore, a highly accurate statement of the horse's mood can be made.

For example, the body as such can be captured, i.e., the overall posture of the horse. The neck can be analyzed by sensors as to whether it is in a raised or lowered position. According to the disclosed method the ears are analyzed by sensors as to whether they are flattened back, pricked forward, synchronously or differently aligned. The tail can be analyzed as to whether it is upright or hanging down. The horse can be checked as to whether it stamps its legs. Monitoring the eyes by means of suitable sensors may be provided to capture an extensive rolling of the eye so that almost only the white of the eye is visible. The movements of the mouth can also be monitored as to whether the mouth is opened wide, which, for example, corresponds to a threatening posture of the horse. The entire body tension, i.e., the tonus, can also be captured by sensors, and further, in a manner which is known in the art, the respiration and the respiratory sounds of the horse can play a role and can be captured by sensors. In total, the horse's moods, such as tension, relaxedness, anger, subservience, doziness, mistrust, disease or excitement can be derived from the captured physiological data.

For example, if the head is shaken sideways vigorously or performs rapid upward movements, the horse feels disturbed. If the head is repeatedly ducked down shortly, the horse is curious. If the nostrils move from side to side, the horse wants to cheer up. If the horse nudges with its head, it wants to start moving or to attract attention. With its mouth open, however, the horse is aggressive. If the head is turned away, this means a rejection.

The legs can be analyzed to capture the mood, too: If the front legs move jerkily forward, this represents a threatening posture of the horse. If the hind leg is lifted, then the horse is ready to kick. To throb with one leg or to stamp means that the horse feels harassed. If the horse paws with its legs or hooves, respectively, this allows to conclude on the horse's frustration.

Whether, for example, chewing movements are performed that are suggestive of subservience or whether loosely hanging lips signal a relaxedness of the horse can be captured by monitoring the horse's mouth.

In particular when multiple horses are configured with appropriate sensors and the body posture of the horses can be detected not only individually, but in relation to each other, it is possible to analyze, for example, whether the horse builds up the above mentioned body lock against another horse and shows dominance and whether this mood of the horse is possibly supported and strengthened by shoulder bumps, or whether, for example, a horse shows the other one its backside to signal that it wants to be left alone.

A particularly simple statement concerning the horse's mood, which can be implemented for example—as mentioned above—in simple graphical, such as color-coded, signals, consists of determining a stress level of the horse in the form of a top level mood, as will be explained in more detail later in reference to FIG. 3. For this purpose, components of the horse's body language which signal tension and relaxedness are taken into consideration, where the positions, or movements, respectively, of ears and tail, as well as the horse's neck can preferably be combined with the behavior of the animal, such as standing, forward or backward movement, rearing and the like.

Preferably, an electronic unit, which may preferably be provided with an external sensor, can be used for capturing the data captured by sensors. This unit comprises evaluation electronics for the sensor signals, a separate power supply, and a radio module, which uses, for example, a common wireless standard such as Bluetooth, Zigbee, GSM, or the like. The external sensor is connected by means of, for example, four wires to an expansion plug of the electronic unit. The electronic unit is placed in the horse's head or forehead region and the external sensor for capturing the ear position or ear movement, respectively, is attached to one ear, for example, using the ear protectors which are commercially available and already widely used with horses and to which the external sensor can be fastened easily. Preferably a combined accelerometer/magnetometer can be used as external sensor, since such sensors are available inexpensively, are of small physical dimensions and allow measurement signals of high accuracy.

In a preferred embodiment of the method data concerning the position and movement of the tail can be captured as well, for example by using a second electronic unit, which is fastened in the region of the horse's back or the tail, respectively. This is not disagreeable for the horse and does not lead to unusual movements of the tail, since it is common, for example, to run leather straps under the root of the tail, so that accordingly applying a sensor in this area is as unproblematic for the horse as is applying a sensor to the ears using the ear protectors which are used in practice anyway.

In a particularly simple and inexpensive preferred embodiment of the disclosed method it is provided to perform the analysis of the horse's body language by exclusively using the sensors on ears and tail, so that, for example, even when monitoring a larger number of horses, the data volume can preferably be kept small, and accordingly for example, a central server, which may be located in the office building of a stable, can process the corresponding amounts of data without problems.

BRIEF DESCRIPTION OF THE DRAWINGS

In the following the disclosed method is explained in detail with reference to purely schematic drawings.

DETAILED DESCRIPTION OF THE PREFERRED EMBODIMENTS

Figure 1:
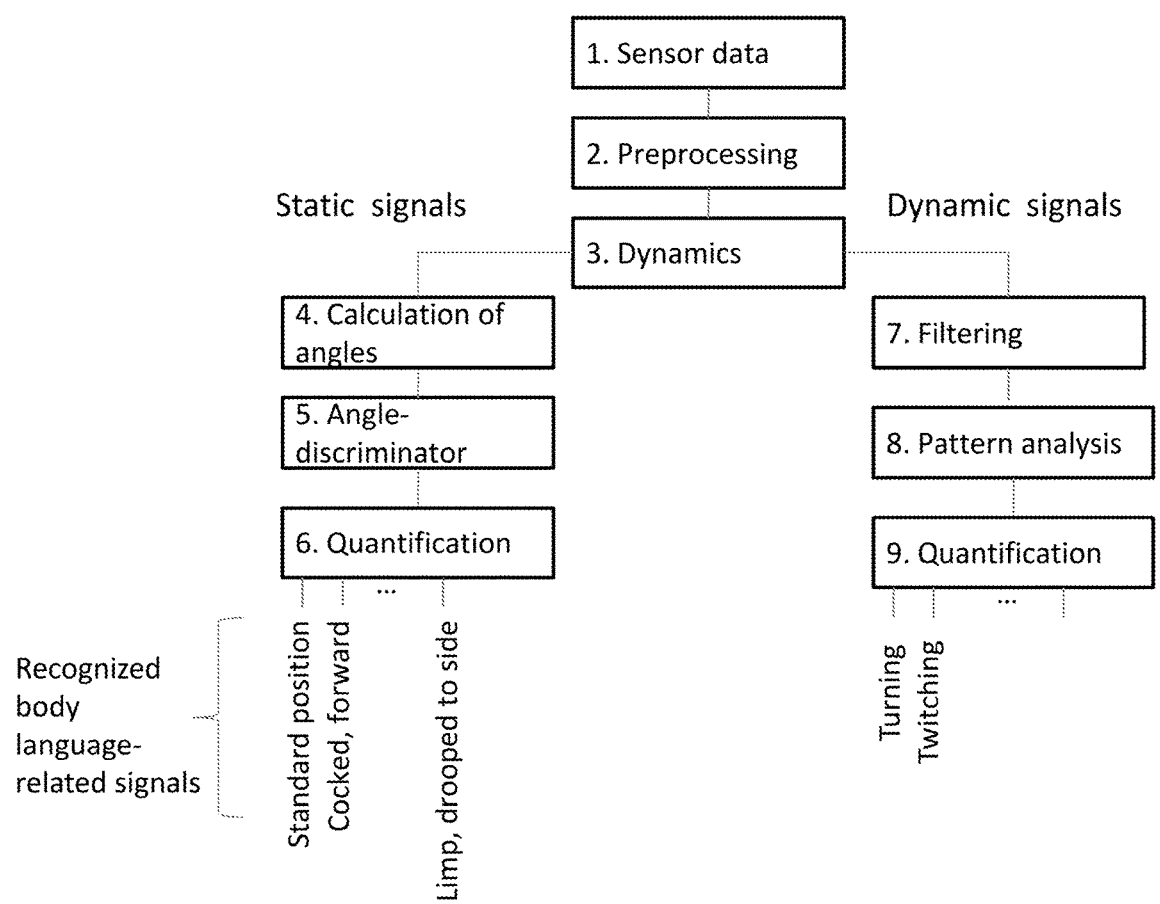
FIG. 1 illustrates a procedure for the recognition of body language-related signals by means of sensor data, exemplified by a horse's ears.

As already mentioned above, the implementation of sensor information into moods is accomplished in several steps. First, the different body language-related signals must be recognized by means of the sensor data. Then, each of the recognized body language-related signals is quantified. In a further step of processing these values are converted into detailed emotions and tempers. More comprehensive statements such as the well-being are calculated from these individual moods. In FIG. 1 the procedure for recognizing body language-related signals by means of sensor data is described, exemplified by the ears. The terms employed and their meanings are:

1. Sensor data: In order to determine angles in all three spatial dimensions (yaw, pitch, roll), a combination of at least a 3-axis-accelerometer and a 3-axis-magnetometer is required. Because in this example the position of the ears in relation to the head is of interest, one such combination each is provided on the head and on the ears, respectively.
2. Preprocessing: In addition to various noise reduction filters the difference between head and ear sensors is calculated.
3. Dynamics: A further analysis distinguishes between static and dynamic signals. In order to achieve this, the variance of the data channels is calculated for example. Depending on this result further processing is carried out in the static or in the dynamic branch of the analysis, respectively.
4. Calculating the angles: In the static part of the analysis the angles (yaw, pitch, roll) are calculated from the accelerometric and magnetometric data.
5. Angle discriminator: For each of the static body language-related signals there is a separate discriminator, in which the valid range is described by means of minimum and maximum angles for each of the 3 angles in space. If all angles are within the valid range, a corresponding signal is generated and the body language-related signal is displayed as having been recognized.
6. Quantification and standardization: In this step the recognized body language-related signal is quantified. The distance of the current angle to the threshold angles is one criterion for this, another is the time period within the valid range. Thereafter the value is standardized for the respective time period.
7. Filtering for dynamic signals: For the subsequent pattern recognition additional filter operations are necessary. These can either be moving average filters or filters that calculate the difference or the sum of the data channels.
8. Pattern analysis: For each of the dynamic body language-related signals a separate pattern exists. A correlation analysis is used for signals with a relatively constant time window, e.g. twitching of the ears. A typical set of measurements of the pattern to be looked for is used as pattern. For less well defined movements a descriptive analysis is employed: for example, the pattern is defined by a minimal and maximal chronological sequence of extreme values in the various data channels and the levels lying in between.
9. Quantification and standardization of the dynamic signals: For quantification one or more extreme values in one of the data channels within the found pattern is used. The frequency within a time interval is a further criterion. Thereafter the value is standardized for the respective time period.

Figure 2:
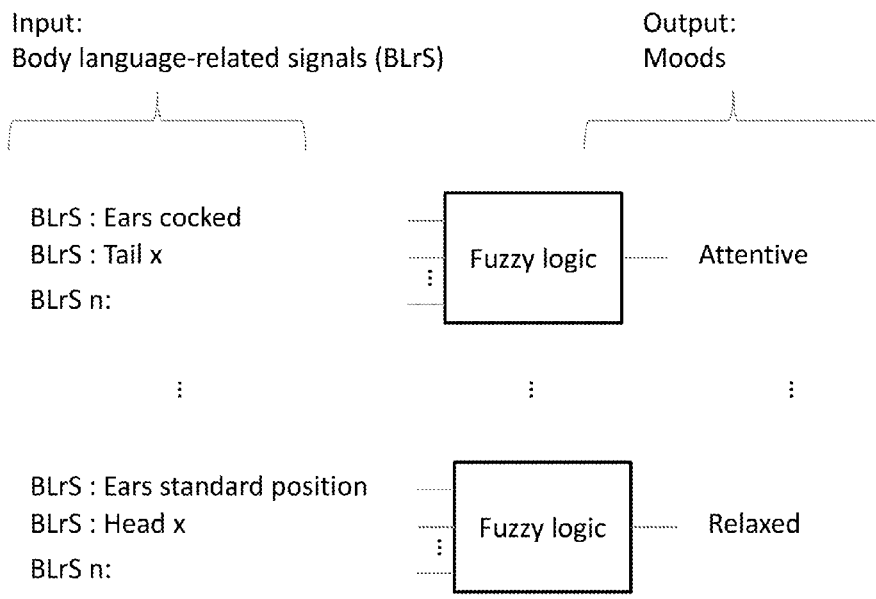
FIG. 2 illustrates the detection of moods by means of body language-related signals.

FIG. 2 explains the detection of moods by means of body language-related signals. Here, the body language-related signals from different areas, such as ears, tail, head, neck are summarized. This is done for example with fuzzy logic modules. For each mood specific membership functions and rules are defined. A rule is of the form: If "ears pricked up" ="strong" and "tail high" ="strong" then "attention" ="high". Implementing the quantified body language-related signals into the meaning "strong" is carried out by the membership functions. The output of these modules, the mood, is represented as a probability value between 0 and 1.

Figure 3:
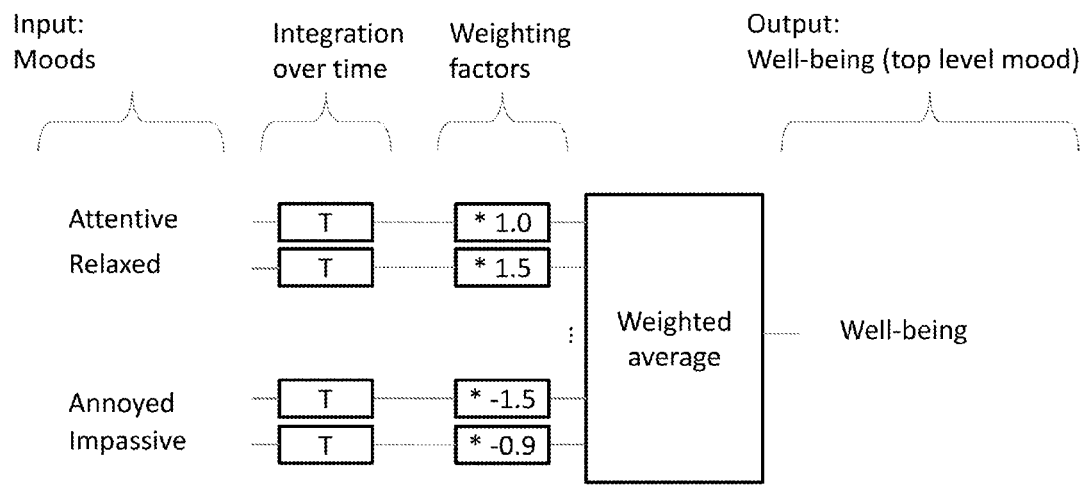
FIG. 3 illustrates the detection of top level moods (TLM) exemplified by "well-being"

In a third processing step the different moods are combined to a top level mood (TLM). The purpose of this TLM is to provide a quick overview of the state of the horse, for example by a color code. The detection of top level moods (TLM) is exemplified in FIG. 3 for the term "well-being".

Individual moods are integrated over time and summarized as weighted input signals to a mean value. The weighting depends on the TLM module and can be positive as well as negative. Alternatively, this processing step can also be calculated by the fuzzy logic process described in FIG. 2.

In the process described above, the mood is calculated according to standards that are more or less valid for all horses. Sometimes it is desirable, however, to adapt the analysis to a greater extent to an individual. This can happen, for example, by summarizing the body language-related signals which were quantified according to the method described in FIG. 1 at a point in time to form a feature vector. In parallel, the mood of interest is assessed by an expert and included in the analysis. By principle component analysis the relevant body language-related signals can then be identified for the selected mood. The remaining steps are as described.

Figure 4:
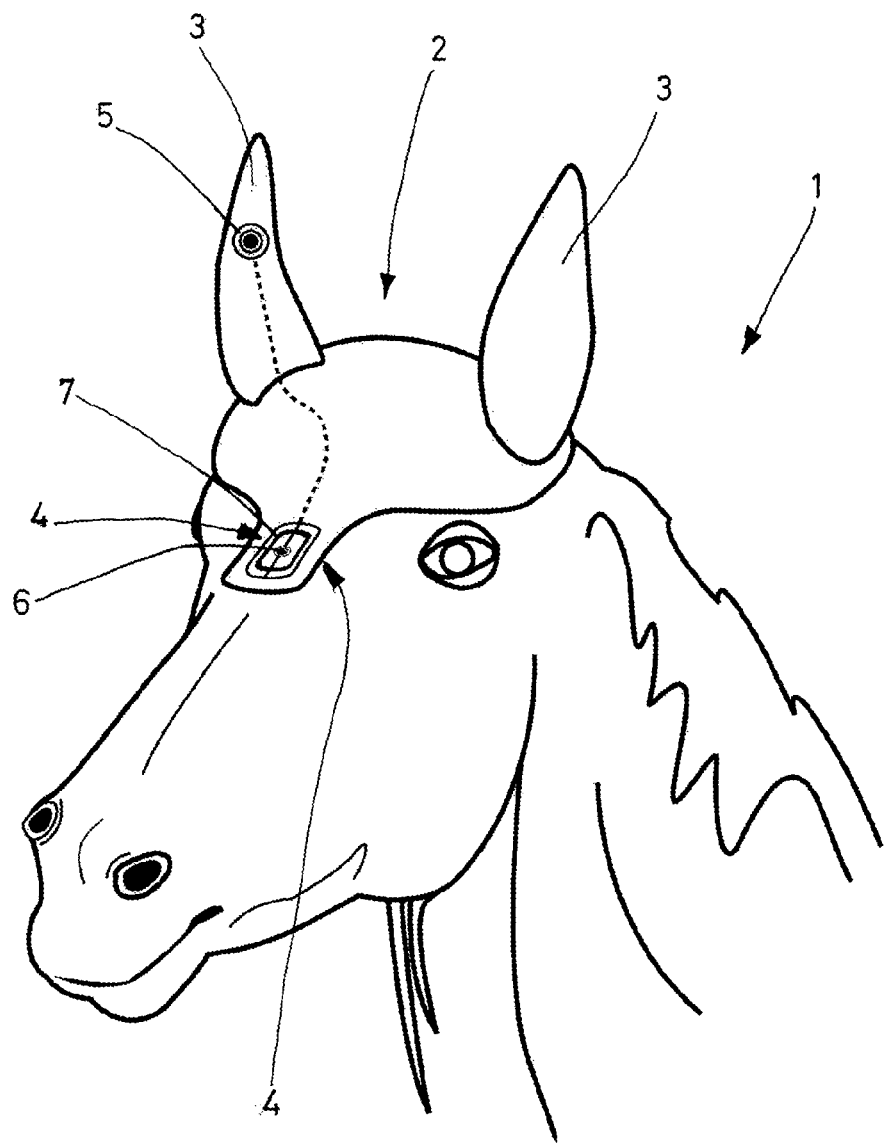
FIG. 4 illustrates a device, the use of which allows one to perform the disclosed method.

In FIG. 4 an only partially illustrated horse is designated by 1, carrying an ear protector 2, which covers both ears of the horse with an ear cap 3 each. Between the ears the ear protector 2 forms a frontal lobe 4.

Merely by way of example a sensor 5, which captures the position or movement, respectively, of the respective ear, is illustrated in only one of the two ear caps 3. Actually such a sensor 5 may be provided in each of the two ear caps 3.

A further sensor 6, through which the position or movement, respectively, of the head can be detected, is provided on the frontal lobe 4. Thus, by comparing the movements of the head on the one hand, and the ears on the other hand the position of the ears on the head can be calculated precisely so that, accordingly, a statement concerning the particular mood of the horse is enabled or supported.

Furthermore, an electronic unit 7 to which the sensor data from sensors 5 and 6 are fed is provided in the frontal lobe 4. The corresponding connection to sensor 5 is indicated by dashed lines, where this connection can be configured in a wired or a wireless manner.

The electronic unit 7 can be used for temporarily storing the sensor data so that these data can be read out later. The sensor data can then, accordingly, be evaluated externally. Alternatively, the evaluation can be performed in the electronic unit 7 already, so that the transmitted data volume can be reduced considerably.

The electronic unit 7 may include a transmitter which transmits the data, be it the raw data or the results of the evaluation, automatically to a relay station. This relay station may be provided in the stable or in a pasture or paddock and may serve to transmit the data to a receiver.

The receiver can be a "final recipient" such as a trainer, veterinarian or horse owner, to whom the statement concerning the horse's mood is transmitted. In particular, this statement can be transmitted to several "final recipients".

Or the recipient may be a central computer, which is for example located on the corresponding stud or horse farm, where the particular horse is situated, or which is provided with a computer program designated as "expert system" to evaluate the sensor data.

The above mentioned central computer can be used to evaluate the raw sensor data and/or to automatically transmit, via a connection to the Internet, a mobile network or the like, the raw data or the statement concerning the horse's mood, respectively, to the above mentioned "final recipient".

It may alternatively be provided not to perform the evaluation of the transmitted data until they reach the final recipient, for example as an application that runs on a smartphone.

The invention claimed is:

1. A method for determining moods of a horse, comprising the steps of:

determining, by a plurality of sensors, physiological parameters of the horse, including determining at least one of a movement and position of at least one ear of the horse, wherein one of the sensors used for determining the at least one of a movement and position of the at least one ear is a motion sensor determining intensity of movement and/or orientation in space of the at least one ear, the motion sensor being one of a magnetic field sensor and an acceleration sensor, and determining at least one of a movement and position of the head of the horse and calculating the at least one of a movement and position of the at least one ear relative to the head;

recognizing and quantifying body language signals mediated by the at least one of a movement and position of the at least one ear relative to the head determined in said step of determining; and outputting a statement derived from the determined physiological parameters indicating the moods of the horse.

2. The method of claim 1, wherein said step of determining further comprises determining at least one of a movement and position of the tail of the horse by the sensors.

3. The method of claim 2, wherein a sensor for determining a position of the tail is disposed on a root of the tail.

4. The method of claim 1, wherein the magnetic field sensor is used as the motion sensor to determine the intensity of movement and/or orientation in space of the at least one ear.

5. The method of claim 1, wherein the acceleration sensor is used as the motion sensor to determine the intensity of movement and/or orientation in space of the at least one ear.

6. The method of claim 1, wherein a sensor for determining the position of the at least one ear is installed in an ear protector placed on the at least one ear of the horse.

7. The method of claim 6, wherein a sensor for determining at least one of a movement and position of the head is installed in the base of said ear protector.

8. The method of claim 1, wherein the statement is provided in a differentiated manner for different moods of the horse.

9. The method of claim 1, wherein the statement is provided as a summary by taking into account a plurality of different moods determined over a time period and determining a summarized mood based on a weighting of the different moods.

10. A device for capturing moods of a horse, comprising:

a first sensor attached to one of an ear clip or an ear protector, the sensor determining at least one of a position and movement of the ear, a second sensor configured to be placed on a head of the horse proximate the ear to determine at least one of movements and position of the head, and an electronic unit evaluating the sensor data, the electronic unit configured to receive signals from the first sensor and the second sensor indicating the determined at least one a position and movement of the ear relative to the head and to recognize and quantify the body language signals mediated by the ear.

* * * * *